(12) United States Patent
Tipper et al.

(10) Patent No.: US 9,448,152 B2
(45) Date of Patent: Sep. 20, 2016

(54) SUSPENDED SOLIDS TEST DEVICE AND METHOD

(71) Applicants: Mark James Tipper, Christchurch (NZ); Martin Robert Clay, Christchurch (NZ)

(72) Inventors: Mark James Tipper, Christchurch (NZ); Martin Robert Clay, Christchurch (NZ)

(73) Assignee: Mark James Tipper (NZ)

( * ) Notice: Subject to any disclaimer, the term of this patent is extended or adjusted under 35 U.S.C. 154(b) by 0 days.

(21) Appl. No.: 14/403,559

(22) PCT Filed: Jun. 5, 2013

(86) PCT No.: PCT/IB2013/054612
§ 371 (c)(1),
(2) Date: Nov. 24, 2014

(87) PCT Pub. No.: WO2013/190418
PCT Pub. Date: Dec. 27, 2013

(65) Prior Publication Data
US 2015/0124248 A1 May 7, 2015

(30) Foreign Application Priority Data

Jun. 20, 2012 (NZ) .......................... 600754
May 14, 2013 (NZ) .......................... 610591

(51) Int. Cl.
*G01J 1/10* (2006.01)
*G01N 15/06* (2006.01)

(52) U.S. Cl.
CPC ....... *G01N 15/06* (2013.01); *G01N 2015/0687* (2013.01)

(58) Field of Classification Search
CPC .................... G01N 15/06; G01N 2015/0687
USPC .............. 356/243.2, 237.1, 240.1, 415, 410, 356/432–442, 249
See application file for complete search history.

(56) References Cited

U.S. PATENT DOCUMENTS 2,489,723 A * 11/1949 Resnick ............... G01N 21/293
356/412

* cited by examiner

*Primary Examiner* — Tri T Ton
(74) *Attorney, Agent, or Firm* — Galbreath Law Offices, P.C.; John A. Galbreath

(57) ABSTRACT

A Total Suspended Solids (TSS) Device which includes a plurality of calibrated sample containers in a case, such that each calibrated sample container contains a calibrated sample, wherein each calibrated sample is a sample with a known suspended solids concentration prepared from a site sample, such that said TSS device is configured to allow a discharge sample in a discharge sample container to be visually compared to each of the calibrated samples in the calibrated sample containers in said case, where the discharge sample is a sample of a liquid discharge from a site.

28 Claims, 3 Drawing Sheets

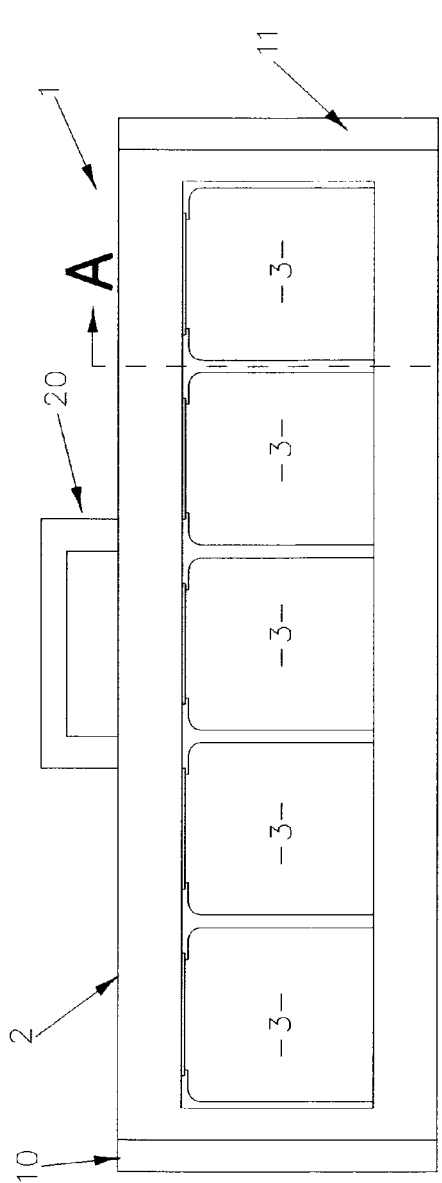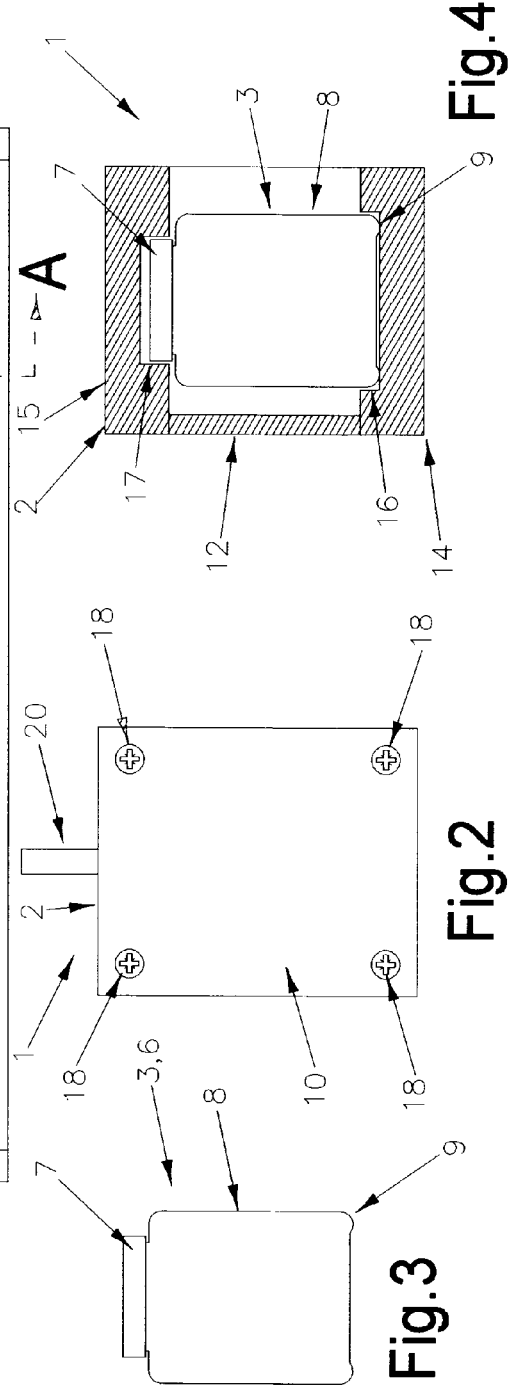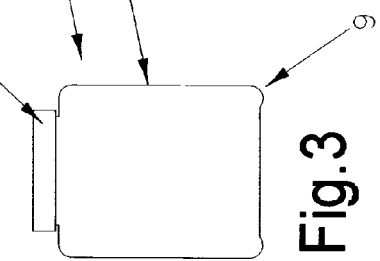

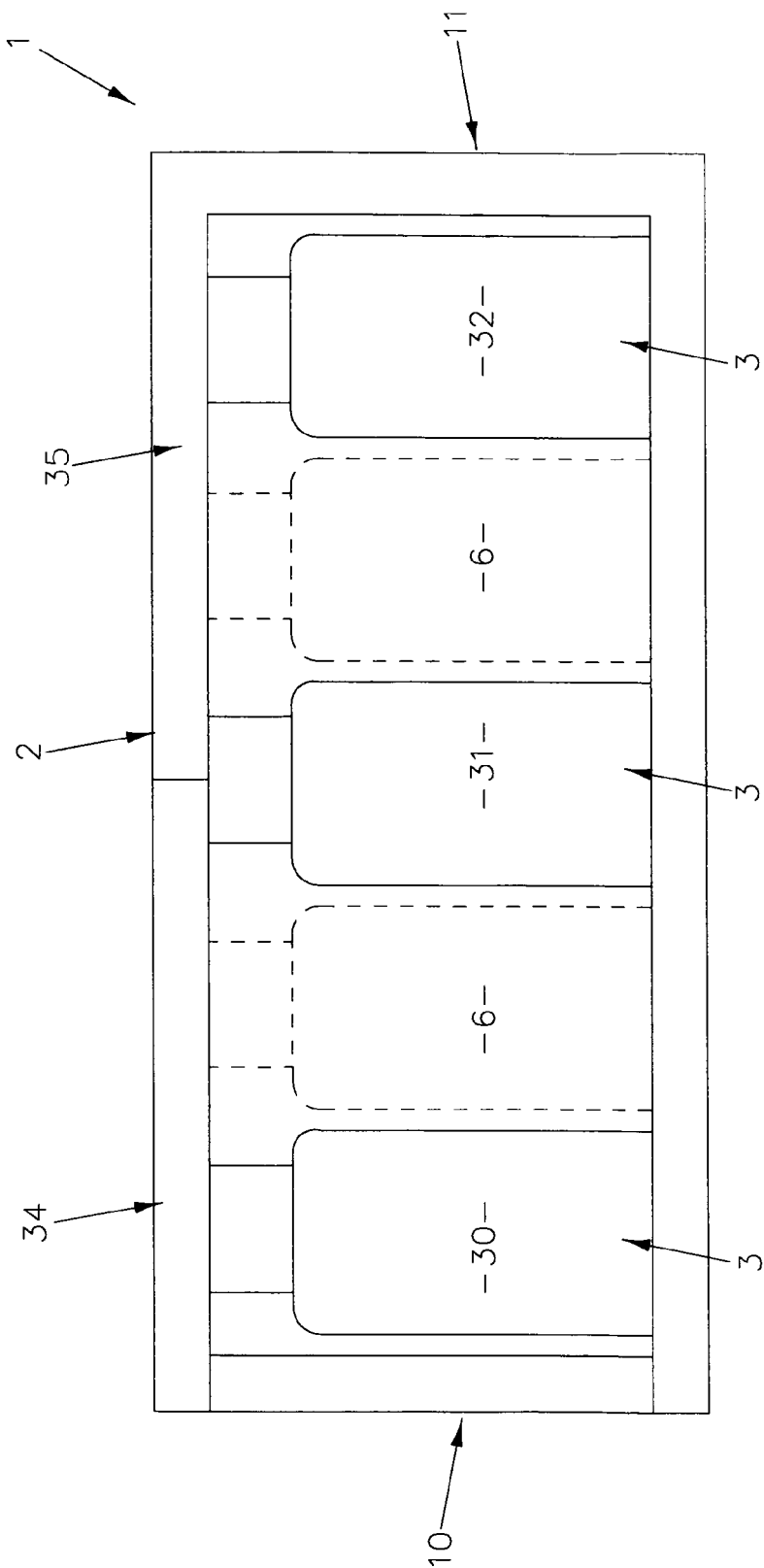

SUSPENDED SOLIDS TEST DEVICE AND METHOD

TECHNICAL FIELD

The present invention is a device and method for measuring the suspended solids concentration in a liquid, particularly site discharge, runoff or storm water.

BACKGROUND ART

When construction work is undertaken the land is often disturbed and there may be a runoff or discharge which enters the storm water system or existing water courses, lakes or other water bodies. The concentration of various contaminants, including suspended solids needs to be controlled to prevent downstream detrimental effects. To do this governmental bodies place limits on the concentration of contaminants allowed in the discharge. To meet these standards those creating the discharge put in place measures to meet these concentration limits, but to ensure they are complied with testing needs to occur.

To measure the concentration of suspended solids in a laboratory the sample is often allowed to settle for a predetermined time to remove certain settleable material then filtered, normally through a glass filter with around 1.2 micrometer pore size to separate the suspended solids. The glass filter is weighed before filtering and then the retained material and filter dried to constant mass before reweighing and calculating the suspended solids. This method takes time and requires a skilled laboratory technician. For runoffs and discharges over a short timeframe (1 to 5 days) the cost and time taken make this method less than ideal, and it is very unlikely to be carried out on site.

Turbidity can be used as an indication of suspended solids but each discharge has specific characteristics, and a calibration curve relating the turbidity (optical obscuration) to the suspended solids loading in each specific discharge is required. Solids and other fine suspensions affect the turbidity though may not increase the suspended solids loading significantly.

There are turbidity meters available but these in general come with a high cost ($2000+) and require a separate calibration curve for each individual discharge. This may be justified for long term projects or wastewater/sewage plant discharges but for short term discharges it is neither cost effective nor practical. Further problems with the use of turbidity probes include recalibration if the discharge changes properties, keeping the probes clean and general maintenance of the equipment. Additionally the meters may be complicated to calibrate and use, and there use may be beyond the technical competence of some field staff.

Any discussion of the prior art throughout the specification is not an admission that such prior art is widely known or forms part of the common general knowledge in the field.

It is the object of the present invention to provide a suspended solids test device that overcomes at least one of the deficiencies in existing measures or provides the consumer with a useful choice.

DISCLOSURE OF INVENTION

The present invention provides a Total Suspended Solids (TSS) Device which includes a plurality of calibrated sample containers and a case, such that the case is configured to retain and protect each of the calibrated sample containers and each calibrated sample container contains a calibrated sample, wherein each calibrated sample is a sample with a known suspended solids concentration prepared from a site sample such that said TSS device is configured to allow a discharge sample in a discharge sample container to be visually compared to each of the calibrated samples in the calibrated sample containers, where the discharge sample is a liquid sample of the discharge from a site.

Preferably the optical comparison is a manual visual comparison carried out by a user of the TSS device.

Preferably the site sample is a liquid site specific sample. In a preferred form the liquid site sample has a total dissolved solids concentration greater than or equal to all of the calibrated samples required. Preferably each calibrated sample is prepared by diluting the site sample with water. Preferably the water is deionised. Preferably each calibrated sample is stabilised to inhibit microbiological or fungal growth. In a highly preferred form an algaecide or biocide is added to stabilise each calibrated sample. Preferably said stabilisation includes ultra violet light treatment.

In an alternative preferred form the site sample is one or more solid samples. Preferably the or each solid sample is processed then suspended in water to prepare each calibrated sample. Preferably the water is deionised.

Preferably the case includes a diffuser configured to provide a neutral background for viewing the calibrated samples and/or diffuse light passing through each calibrated sample container and the discharge container.

In a preferred form there are three calibrated sample containers, a first calibrated sample container, a second calibrated sample container and a third calibrated sample container, such that each of the first and third calibrated sample containers is located immediately adjacent one opposite end of the TSS device, with the second calibrated sample container located between the first and third, such that the spacing between adjacent calibrated sample containers is sufficient to allow a discharge container to be inserted between. Preferably the second calibrated sample container contains a calibrated sample with a predetermined maximum site concentration of total suspended solids allowable in the discharge sample. Preferably the concentration of total suspended solids in the first calibrated sample container is the lowest and the concentration of total suspended solids in the third calibrated sample container is the highest. Preferably the first calibrated sample container is labelled 'PASS' and the third calibrated sample container is labelled 'FAIL'. Preferably the second calibrated sample container is labelled 'LIMIT'.

Preferably the concentration of total dissolved solids in each of the calibrated sample containers is selected from the group consisting of 1%, 5%, 10%, 20%, 33%, 50%, 66%, 100%, 110%, 125%, 133%, 150%, 200%, 400%, 600%, 800%, 1000%, 20000%, or any value between, where 100% is the predetermined maximum site concentration of total suspended solids allowable in the discharge sample.

Preferably the site sample undergoes at least one pre-treatment step to prepare said calibrated sample. Preferably each pre-treatment step is independently selected from the list consisting of filtration, dilution, the addition of an additive, physical treatment and resuspension. Preferably the physical treatment could be agitation, settling etc. Preferably the site sample pre-treatment includes additional steps which may be required to reflect any site specific treatment of the runoff prior to discharge.

Preferably there are at least two calibrated sample containers, each with a different suspended solids sample. In a highly preferred form there are between three and six calibrated sample containers, each with a different suspended solids concentration.

The present invention also provides a method for using the TSS device which includes the following steps in order:
A1. Prepare site sample.
A2. Compare prepared site sample to calibrated sample.

BRIEF DESCRIPTION OF DRAWINGS

By way of example only, a preferred embodiment of the present invention is described in detail below with reference to the accompanying drawings, in which:

FIG. 1 is a side view of the Total Suspended Solids device, hereinafter TSS Device;

FIG. 2 is an end view of the TSS Device;

FIG. 3 is a side view of a sample container;

FIG. 4 is a cross-sectional view of the TSS device in the direction of the arrows A-A;

FIG. 6 is a side view of a second embodiment of the TSS Device.

Figure 5:
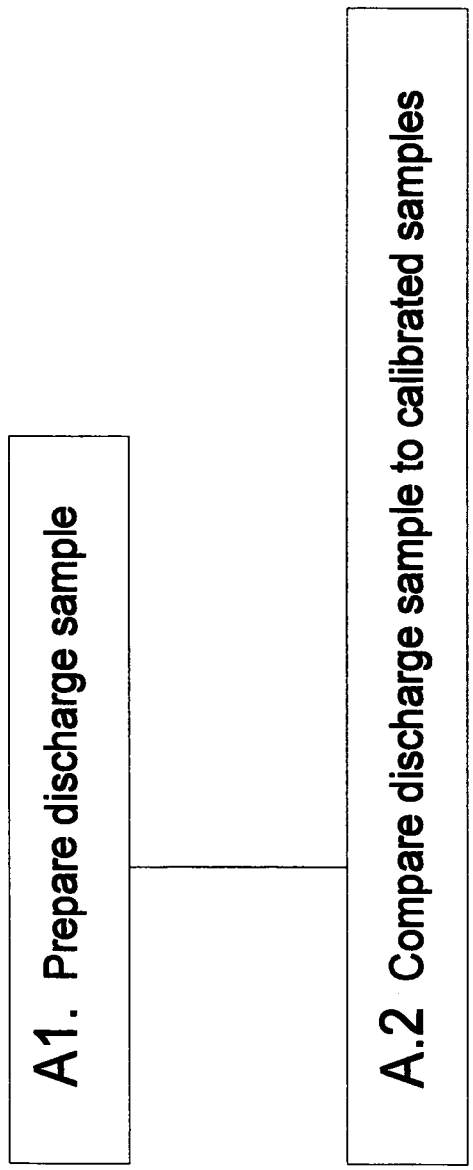
FIG. 5 is a flow chart of a method of using the TSS device.

There has long been a need for a simple low cost device for determining suspended solids levels that can be carried out quickly onsite yet the laboratory testing and turbidity probes are the methods most commonly used.

BEST MODE FOR CARRYING OUT THE INVENTION

Referring to FIGS. 1 and 2 a Total Suspended Solids (TSS) device (1), hereinafter just called a TSS device (1), is shown. The TSS device (1) includes a case (2) and five calibrated sample containers (3), though there may be as few as 2 or more than 5 calibrated sample containers. The case (2) is designed and dimensioned to protect and retain the calibrated sample containers (3).

FIG. 3 shows a sample container (3,6), either a calibrated sample container (3) or a discharge sample container (6). Where the discharge sample container (6) is used to collect and/or retain a sample of the discharge to be compared to a calibrated sample within each of the calibrated sample containers (3). Each calibrated sample contains a known concentration of suspended solids.

Each sample container (3,6) includes a removable cap (7) designed to seal the sample container (3,6). In the configuration shown each of the sample containers (3,6) is a rectangular container which includes at least one window (8), a cap (7) and a container base (9). The window (8) is for viewing a sample within a sample container (3,6), and the cap (7) is a removable closure located at one end of the sample container (3,6) used to seal the sample container (3,6). The container base (9) is the end of the container opposite the cap (7). In the simplest embodiment each of the sample containers (3,6) is a clear and essentially colourless rectangular plastic jar of known type, the whole of the sample container (3,6) effectively being the window (8).

The dimensions of each of the sample containers (3,6) is similar or the same, though for some applications they may simply have similar optical path lengths. Where the optical path length is the length of a path that light follows through the sample from one side of the sample container (3,6) to the other. It is preferred that the sample containers (3,6) are all the same.

The case (2) includes, two ends (10, 11), a diffuser (12), a base (14) and a top (15).

Referring to FIG. 4 a cross sectional view of the TSS device (1) is shown. with the base (14) including a base channel (16) which is a channel parallel to the length of the base (14) dimensioned to retain container base (9). It should be noted that dimensions of the base channel (16) are not so close to those of the container base (9) dimensions so as to prevent all movement of a calibrated sample container (3) within said base channel (16).

Also referring to FIG. 4 the top (15) is shown to include a top channel (17) which is a channel parallel to the length of the top (15) dimensioned to retain the cap (7). It should be noted that dimensions of the top channel (17) are not so close to those of the cap (7) dimensions so as to prevent all movement of a calibrated sample container (3) within said top channel (17).

The diffuser (12) is a piece of material intended to provide a uniform background to view the contents of the calibrated sample containers (3) and diffuse the light. The diffuser (12) forms part or all of one side of the case (2). Suitable materials include translucent or transparent plastic materials with a film of uniform colour applied, translucent materials, translucent and transparent glass, etc.

When in place within said case (2) each of the calibrated sample containers (3) is alongside at least one other calibrated sample container (3). The base (14), top (15) and the two ends (10, 11) are releasably attached to each by retention means (18) of a known type, for example screws, bolts, clips, hook and loop connectors, magnetic clips etc. The case (2) is configured to protect and retain the calibrated sample containers (3) for use.

To prepare the TSS device (1) for use a sample of the soil or raw contaminated water is collected. This sample is used to prepare the contents of the calibrated sample containers (3), each of the calibrated sample containers (3) carries a different total suspended solids concentration made up from the sample provided. The proposed method of preparing the contents will be discussed later. The TSS device (1) is then assembled and sealed with tamper evident labels or similar tamper evident devices to preserve the integrity of the calibrated samples (3). The permit will specify an allowable level of total suspended solids within the discharge or runoff, this limit value will be used to set the total suspended solids concentration in at least two of the calibrated sample containers, one being above and the other being below the limit. Noting that in some cases the permit may not specify total suspended solids, in these cases it may be possible to calculate the maximum allowable total suspended solids, or obtain separate documentation specifying the total suspended solids allowed.

In this embodiment the case (2) includes a handle (20) attached to the exposed surface of the top (15) to allow the TSS device to be easily carried. This handle can be any known handle, for example be a rigid handle either fixed or hinged, a flexible handle attached by loops or similar etc.

One method of assembling the TSS device (1) is as follows:
a. The base (14) is attached to the first and second ends (10, 11);
b. Each of the calibrated sample containers (3) is placed into the base channel (16), normally in increasing concentration order;
c. The top (15) is fixed to the first and second ends (10, 11), with the cap (8) retained within the top channel (17);
d. Tamper evident labelling or devices are applied.

To prepare the calibrated sample to be contained within each of the calibrated sample containers (3) a sample of the soil, ground or raw contaminated water from the site (the site sample) is obtained. This site sample will normally be provided by the person seeking permission for the discharge or runoff. For clarity where the sample is the raw contaminated water from the site it will be referred to as a liquid site sample, and where it is a solid sample such as soil or ground material from the site it will be referred to as a solid site sample.

Initial procedures used to prepare the calibrated samples are likely to be as follows, but the optimum process will depend on the suspended solids concerned and the discharge water/runoff properties.

Upon receipt of the sample a first stage is undertaken. This first stage is likely to include one or more of the following:
  i. Agitate a liquid site sample to re-suspend solids within the sample, not necessary if a solid sample is provided;
  ii. Filtration/sieving of the site sample to remove material greater than about 0.5 mm (fine sand) as this tends to drop out of suspension quickly. For some applications this may be 1 mm rather than 0.5 mm.
  iii. Gravity settling of a liquid site sample for a short time, say between about 1 minute to 30 minutes, this could be undertaken for a solid site sample if it was suspended in a solvent first;
  iv. Determination of the suspended solids concentration of the site sample, for a solid site sample this may involve suspending it in a suitable solvent, most likely water;
  v. A combination of one or more of steps i, ii, iii and iv.

The next step may involve one or more of the following steps depending on the sample provided:
  vi. Further filtration to remove the suspended solids, though it is uncertain how the suspended solids retained on the filter will all be re-suspended in later steps. Given the pore size used for this step is likely to be around 0.5 micrometers the filter may retain some of the suspended solids which will decrease the accuracy.
  vii. Decolourising, some site samples may need the colour reduced so that an optical comparison can be carried out.
  viii. Drying or other heat treatment.

Many liquid site samples change when concentrated or heated treated and these changes may be irreversible, as such these treatments may not be appropriate. It is believed that some methods of concentrating a liquid site sample will not affect the calibrated samples prepared, for example low temperature vacuum concentration.

Given the site samples can contain microbiological contaminants which over time can grow it is thought that a sterilisation step will be needed for the calibration samples in most cases. The sterilisation step may be ultraviolet (UV) treatment or the addition of a suitable micro-biocide, algaecide or similar additive. The original site sample will not in most cases be kept for any significant period of time so microbiological contamination is unlikely to be a problem, though a biocide and/or algaecide may be added in some cases.

One alternative method of preparing the calibrated samples is described below:
  Obtain soil sample from site;
  Sieve soil sample to remove fraction above about 1 mm (this may be 0.5 mm);
  Autoclave sieved soil sample;
  Suspend known quantity of sieved soil sample in water, with or without additives to form a base calibrated sample;
  Dilute base calibrated sample to prepare the required calibrated samples.
  Transfer calibrated sample to calibrated sample container (3), this step is unnecessary if the calibrated sample is prepared in the calibrated sample container (3).

Each of the calibrated sample containers (3) is labelled with the suspended solids concentration contained within that calibrated sample container (3), and/or the case (2) is temporarily or permanently marked with the suspended solids concentration of the calibrated sample container (3) closest to that label/marking.

The object is to prepare a number of calibrated samples directly from the soil (solid site sample) or, preferably, the untreated raw discharge or runoff (liquid site sample), at the location in question. As each calibrated sample container (3) has a known concentration of suspended solids from the location in question, in a form able to be optically compared directly with a site sample of the discharge water or runoff on site, a rapid determination can be made as to whether the limits set are being maintained. It should be noted that the comparison is made manually, that is by the user directly without the use of electronic aids and this is the preferred approach in most cases.

It has been found that preparation of the calibrated samples directly from certain solid site samples can be unreliable and as such the preferred method is to prepare the calibrated samples from a liquid site sample.

For example, the calibrated sample for each calibrated sample container (3) is preferably prepared in the following way.

A liquid site sample is collected from the site, and the total suspended solids is determined by a suitable standard method, such as APHA Method 2 540-D.

If the liquid site sample has a concentration of total suspended solids below that required for the preparation of the calibrated samples then a replacement liquid site sample must be obtained. It should be noted that in some cases it may be possible to concentrate a liquid site sample sufficiently to prepare the calibrated samples.

The calibrated samples are made up from the liquid site sample by taking a predetermined volume of the liquid site sample and adding it to a preset amount of deionised water. Each calibrated sample is stabilised by the addition of a small amount of a known algaecide. Please note that water rather than deionised water can be used, and the water may be added to the liquid site sample. It should also be noted that for some samples it may be necessary to prepare a diluent with similar properties (surface tension, density, viscosity, pH, conductivity, colour, etc.) to the liquid site sample, for example where the site sample has a high dissolved solids concentration.

For completeness the following equation can be used to determine the volume of liquid site sample to add to each calibrated sample container (3).

$$V_{SS} = (C_{CSC} * V_{CSC}) / C_{SS}$$

where:
$V_{SS}$=the volume of site sample to be added to the calibrated sample container;
$C_{CSC}$=the concentration required for this calibrated sample container (3);
$V_{CSC}$=the volume of calibrated sample to be prepared within said calibrated sample container (3); and
$C_{SS}$=the concentration of total suspended solids in the site sample.

The predetermined amount of liquid site sample must be a representative sample and one way of ensuring this is to take the volume of site sample to be added to the calibrated sample container as follows:

i. Pour about 1.5 liters to 2.5 liters of the liquid site sample into a 3 liter beaker;
ii. Stir, using a magnetic stirrer, the contents of the beaker such that the central vortex extends approximately 50% of the depth of the stirred sample depth;
iii. Take the required $V_{SS}$, using a pipette, from a point that is about equidistant from the wall of the beaker and the near edge of the vortex at a depth approximately 50% of the depth of the liquid.

The pipette in step (iii) is most likely to be 25 ml to 50 ml, graduated or fixed volume, but it may be 100 ml.

This method can minimise the amount of solids above a certain predetermined size transferred to the calibrated sample containers (3). Alternative methods of taking the required $V_{SS}$ are well known in the art, they ensure the sample taken is representative of the bulk liquid site sample's total suspended solids loading.

One method of using the TSS device (1) is shown in FIG. 5 and includes steps A1 and A2 as follows:

A1. Prepare discharge sample.
A2. Compare prepared discharge sample to calibrated sample.

Ignoring the standard sampling methods that may be prescribed step A1 includes taking a sample of the discharge or runoff and pre-treating it to obtain a discharge sample that is transferred to a discharge sample container. The pre-treatment may include filtering the sample to remove the fraction above about 1 mm (or possibly 0.5 mm) and/or adding a similar amount of additives to that present in the calibrated samples. No pre-treatment of the discharge sample should be required in most cases; as the discharge sample is collected as close to the point of discharge after any onsite treatment has occurred (such as sediment basin, baffle tank etc.).

In step A2 the contents of the discharge sample container are visually compared to the calibrated sample containers and the concentration of the discharge sample estimated. The comparison simply aims to determine if the concentration is more or less than a particular calibrated sample, the intention is not to determine the actual level of suspended solids but to determine if the discharge permit conditions are being met. If the comparison shows the discharge sample is close to the maximum permitted levels a laboratory test may be needed to determine compliance. It should be noted that it will normally be necessary to agitate the sample containers (3,6) to ensure the total suspended solids have not settled prior to comparison.

In an alternative embodiment the case includes sides attached to each end (10, 11), the base (14) and the top (15), each of the sides has sufficient open area to allow each of the calibrated sample containers (3) to have light passing through them. In this case it may be possible to have some or all of the top (15), the first end (10), the second end (11), the base (14) and the sides permanently attached to other items in the list. For example if all parts of the case (2), except the first end (10), were permanently attached, then the calibrated sample containers (3) could be slid along the channels (16, 17) and the first end (10) then attached.

In further embodiments there are fewer or more calibrated sample containers (3), the number needed depends on the specific needs of the site.

In a preferred second embodiment, shown in FIG. 6, the TSS Device (1) includes three calibrated sample containers (3) each separated by a space sufficient to allow a discharge sample container (6) to be placed between them. The three calibrated sample containers (3) are a first calibrated sample container (30), a second calibrated sample container (31) and a third calibrated sample container (32). The first and third calibrated sample containers (30,32) are located immediately adjacent the first end (10) and second end (11) respectively, with the second calibrated sample container (31) approximately equidistant from each end (10,11). The concentration of suspended solids in the second calibrated sample container (31) is the agreed limit for the site. The concentration of suspended solids in the third calibrated sample container (32), which is to the right of the second calibrated sample container (31) when viewed normally, is above the limit for the discharge. The concentration of the total suspended solids in the first calibrated sample container (30) is below the acceptable discharge limit. By placing the discharge sample container (6) in the space between adjacent calibrated sample containers (3, 30, 31, 32) it is possible to quickly determine if the total suspended solids concentration is above or below the set level. In this form the TSS device (1) is essentially a go/no go (pass/fail) device and it may be labelled this way, a first label (34) indicating 'PASS' and a second label (35) indicating 'FAIL'. The concentration of suspended solids in the first and third calibrated sample containers (30,32) could be 50% and 200%, 10% and 110%, 50% and 110%, 25% and 300% or any other suitable percentage of the total suspended solids concentration in the second calibrated sample container (31).

It should be noted that as the site conditions can change as work is carried out on a site the TSS Device (1) may need to have the calibrated sample containers (3, 30, 31, 32) changed as work progresses. Changes may also occur with water levels, rainfall and drought.

In some embodiments some of the calibrated sample containers may contain calibrated samples used to determine the concentration of something other than the total suspended solids of a sample, e.g. colour, obscuration etc.

In some configurations there is no diffuser (12) in the case (2) but each sample container incorporates a diffuser (12). In other configurations both the case (2) and the sample containers (3,6) include a diffuser (12).

Preparing calibrated samples from the liquid site sample, and visually comparing these to discharge samples in the TSS device (1) has been found to be a rapid and reliable way of determining whether the total suspended solids concentration in the discharge sample exceeds the level set. There has long been a need for a rapid onsite check of total suspended solids levels and the method and TSS device (1) described herein is surprisingly reliable, without the need for an offsite test each time.

In some embodiments there is no handle (20), in others the handle (20) is one or more aperture in the case (2) and in other embodiments the handle (2) is releasably attachable to the case (2).

KEY

1. Total Suspended Solids Device (TSS Device);
2. case;
3. calibrated sample container,
6. discharge sample container;
7. cap (closure for sample container);
8. window (in sample container);
9. container base;
10. first end;
11. second end;
12. diffuser;
14. base;
15. top;
16. base channel (in base);

17. top channel (in top);
18. retention means;
20. handle;
30. first calibrated sample container;
31. second calibrated sample container;
32. third calibrated sample container;

The invention claimed is:

1. A Total Suspended Solids (TSS) Device which includes a plurality of calibrated sample containers in a case, such that each calibrated sample container contains a calibrated sample, wherein each calibrated sample is a sample with a known suspended solids concentration prepared from a site sample, such that said TSS device is configured to allow a discharge sample in a discharge sample container to be visually compared to each of the calibrated samples in the calibrated sample containers in said case, where the discharge sample is a sample of a liquid discharge from a site.

2. The TSS device as claimed in claim 1, wherein the site sample is a liquid site specific sample.

3. The TSS device as claimed in, claim 1 wherein the site sample is a liquid site sample which has a total dissolved solids concentration greater than or equal to all of the calibrated samples required.

4. The TSS device as claimed in claim 1, wherein each calibrated sample is prepared by diluting a representative liquid site sample with water.

5. The TSS device as claimed in claim 1, wherein each calibrated sample is stabilised to inhibit microbiological or fungal growth.

6. The TSS device as claimed in claim 1, wherein an algaecide or biocide is added to stabilise each calibrated sample.

7. The TSS device as claimed in claim 1, wherein each calibrated sample is stabilised to inhibit microbiological or fungal growth and said stabilisation includes treatment with ultra violet.

8. The TSS device as claimed in claim 1 wherein, the site sample is a solid site sample consisting of one or more solid samples from the site.

9. The TSS devices as claimed in claim 1 wherein, the site sample is a solid site sample consisting of one or more solid samples from the site processed to form a processed solid site sample, then a predetermined mass of said processed solid sample is suspended in deionised water to prepare each calibrated sample.

10. The TSS device as claimed in claim 1, wherein there are three calibrated sample containers, a first calibrated sample container, a second calibrated sample container and a third calibrated sample container, such that each of the first and third calibrated sample containers is located immediately adjacent one opposite end of the TSS device, with the second calibrated sample container located between the first and third, such that the spacing between adjacent calibrated sample containers is sufficient to allow a discharge container to be inserted between.

11. The TSS device as claimed in claim 1, wherein there are three calibrated sample containers, a first calibrated sample container, a second calibrated sample container and a third calibrated sample container, such that each of the first and third calibrated sample containers is located immediately adjacent one opposite end of the TSS device, with the second calibrated sample container located between the first and third, such that the spacing between adjacent calibrated sample containers is sufficient to allow a discharge container to be inserted between, such that the second calibrated sample container contains a calibrated sample with a predetermined maximum site concentration of total suspended solids allowable in the discharge sample.

12. The TSS device as claimed in claim 1, wherein there are three calibrated sample containers, a first calibrated sample container, a second calibrated sample container and a third calibrated sample container, such that each of the first and third calibrated sample containers is located immediately adjacent one opposite end of the TSS device, with the second calibrated sample container located between the first and third, such that the spacing between adjacent calibrated sample containers is sufficient to allow a discharge container to be inserted between, such that the concentration of total suspended solids in the first calibrated sample container is the lowest and the concentration of total suspended solids in the third calibrated sample container is the highest.

13. The TSS device as claimed in claim 1, wherein there are three calibrated sample containers, a first calibrated sample container, a second calibrated sample container and a third calibrated sample container, such that each of the first and third calibrated sample containers is located immediately adjacent one opposite end of the TSS device, with the second calibrated sample container located between the first and third, such that the spacing between adjacent calibrated sample containers is sufficient to allow a discharge container to be inserted between, such that the first calibrated sample container is labelled 'PASS' and the third calibrated sample container is labelled 'FAIL'.

14. The TSS device as claimed in claim 1, wherein the concentration of total dissolved solids in each of the calibrated sample containers is selected from the group consisting of 1%, 5%, 10%, 20%, 33%, 50%, 66%, 100%, 110%, 125%, 133%, 150%, 200%, 400%, 600%, 800%, 1000%, 20000%, or any value between, where 100% is the predetermined maximum site concentration of total suspended solids allowable in the discharge.

15. The TSS device as claimed in claim 1, wherein the site sample undergoes at least one pre-treatment step to prepare the calibrated sample.

16. The TSS device as claimed in claim 1, wherein the site sample undergoes at least one pre-treatment step to prepare the calibrated sample and each pre-treatment step is independently selected from the list consisting of filtration, dilution, the addition of an additive, physical treatment and re-suspension.

17. The TSS device as claimed in claim 1, wherein the the site sample undergoes at least one pre-treatment step to prepare the calibrated sample and the pre-treatment step or steps includes additional steps reflecting any site specific treatment of the runoff prior to discharge.

18. The TSS device as claimed in claim 1, wherein there are between three and six calibrated sample containers, each with a different calibrated sample.

19. A method for using the TSS device as claimed in claim 1 which includes the following steps in order:
   A1. prepare the discharge sample; and
   A2. visually compare a prepared discharge sample to a calibrated sample.

20. The TSS device as claimed in claim 1, wherein the case includes a diffuser configured to provide a neutral background for viewing the calibrated samples.

21. The TSS device as claimed in claim 20 wherein the diffuser also is configured to diffuse light passing through each calibrated sample container.

22. The TSS device as claimed in claim 1, wherein the case includes a diffuser configured to diffuse light passing through each calibrated sample container.

23. The TSS device as claimed in claim 21 or claim 22, wherein the diffuser also is configured to diffuse light passing through the discharge container.

24. The TSS device as claimed in claim 1, wherein the case includes a diffuser configured to diffuse light passing through the discharge container.

25. The TSS device as claimed in claim 20 wherein the diffuser also is configured to diffuse light passing through the discharge container.

26. The TSS device as claimed in claim 1, wherein each sample container includes a diffuser configured to diffuse light passing through each calibrated sample container.

27. The TSS device as claimed in claim 26, wherein each sample container includes a diffuser also configured to diffuse light passing through the discharge container.

28. The TSS device as claimed in claim 1, wherein each sample container includes a diffuser configured to diffuse light passing through the discharge container.

\* \* \* \* \*